United States Patent
Zhao et al.

(10) Patent No.: US 9,110,011 B2
(45) Date of Patent: Aug. 18, 2015

(54) REMOTE MEASUREMENT SYSTEM AND METHOD FOR PESTICIDE FOG DISTRIBUTION AND DRIFTING TENDENCY IN AERIAL PESTICIDE APPLICATION

(75) Inventors: Chunjiang Zhao, Beijing (CN); Wengang Zheng, Beijing (CN); Daming Dong, Beijing (CN); Xiande Zhao, Beijing (CN); Changjun Shen, Beijing (CN); Wenbiao Wu, Beijing (CN); Hua Yan, Beijing (CN); Shirui Zhang, Beijing (CN); Feng Bao, Beijing (CN)

(73) Assignee: BEIJING RESEARCH CENTER FOR INFORMATION TECHNOLOGY IN AGRICULTURE, Beijing (CN)

( * ) Notice: Subject to any disclaimer, the term of this patent is extended or adjusted under 35 U.S.C. 154(b) by 62 days.

(21) Appl. No.: 14/234,636
(22) PCT Filed: Oct. 13, 2011
(86) PCT No.: PCT/CN2011/080743
§ 371 (c)(1), (2), (4) Date: Mar. 6, 2014
(87) PCT Pub. No.: WO2013/013448
PCT Pub. Date: Jan. 31, 2013

(65) Prior Publication Data
US 2014/0191130 A1 Jul. 10, 2014

(30) Foreign Application Priority Data
Jul. 25, 2011 (CN) .......................... 2011 1 0209409

(51) Int. Cl.
*G01N 21/35* (2014.01)
*G01N 21/3504* (2014.01)
(Continued)

(52) U.S. Cl.
CPC ............ *G01N 21/35* (2013.01); *G01N 21/3504* (2013.01); *B64D 1/18* (2013.01); *G01N 2021/1795* (2013.01)

(58) Field of Classification Search
CPC ........ G01N 21/35; G01N 21/62; G01N 21/71
See application file for complete search history.

(56) References Cited

U.S. PATENT DOCUMENTS

| 4,777,363 | A | * | 10/1988 | Eiceman et al. | ............... 250/286 |
| 5,628,455 | A | * | 5/1997 | Fukuta | ........................... 239/2.1 |

(Continued)

FOREIGN PATENT DOCUMENTS

| CN | 1260042 | 7/2000 |
| CN | 101694461 | 4/2010 |

(Continued)

OTHER PUBLICATIONS

R. D. Fox, "Visual and Image System Measurement of Spray Deposits Using Water-sensitive Paper", , Applied Engineering in Agriculture. 2003, p. 549-552, vol. 19 (5).

(Continued)

*Primary Examiner* — David Porta
*Assistant Examiner* — Faye Boosalis
(74) *Attorney, Agent, or Firm* — Eagle IP Limited; Jacqueline C. Lui

(57) ABSTRACT

Disclosed are a remote measurement system and method for pesticide fog distribution and drifting tendency in aerial pesticide application, which relate to the technical field of hazardous substance monitoring. The system comprises: a collection module, used for collecting infrared radiation in a detected area, and enabling the infrared radiation to be incident on an optical module; the optical module, used for obtaining, according to the incident infrared radiation, an infrared imaging spectrum in the detected area where a pesticide fog cloud cluster is distributed, and sending the infrared imaging spectrum to a processing module; the processing module, used for analyzing the infrared imaging spectrum, identifying the pesticide fog cloud, obtaining a concentration image of the pesticide fog cloud through inversion, and predicting a drifting tendency of the pesticide fog according to the concentration image. The system and method of the present invention can comprehensively reflect the drifting condition of the pesticide fog in the air in real time, and can obtain the concentration and components of the pesticide fog. The method and system improve the pesticide application efficiency, and prevent damages on the environment and residential areas while saving the cost.

10 Claims, 1 Drawing Sheet

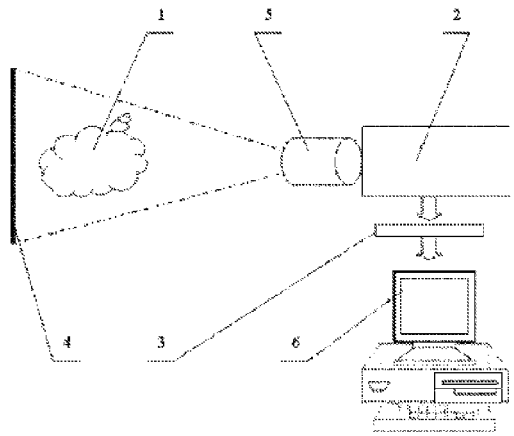

(51) Int. Cl.
  *G01N 21/62* (2006.01)
  *G01N 21/71* (2006.01)
  *B64D 1/18* (2006.01)
  *G01N 21/17* (2006.01)

(56) References Cited

U.S. PATENT DOCUMENTS

2006/0246592 A1  11/2006  Hashmonay
2008/0029702 A1   2/2008  Xu
2012/0223251 A1*  9/2012  Morrow et al. ............ 250/459.1

FOREIGN PATENT DOCUMENTS

CN  102313688   1/2012
WO  2008/081757  7/2008
WO  2011/002272  1/2011

OTHER PUBLICATIONS

Li Cheng Quan, "Research on the Distribution and Visualization of Pesticide Fog Concentration Field in Confined Spaces", Jiangsu University, 2009.

* cited by examiner

Fig. 1

S1 — collecting infrared radiation of a detected area.

S2 — obtaining infrared imaging spectrum of the detected area distributed with pesticide fog clouds based on the incident infrared radiation.

S3 — performing characteristic analysis on the infrared imaging spectrum; identifing the pesticide fog cloud in detected area; inverting concentration image of the pesticide fog cloud; and predicting drift tendency of the pesticide fog cloud based on the concentration image.

Fig. 2

REMOTE MEASUREMENT SYSTEM AND METHOD FOR PESTICIDE FOG DISTRIBUTION AND DRIFTING TENDENCY IN AERIAL PESTICIDE APPLICATION

TECHNICAL FIELD

The present invention generally relates to the technical field of hazardous substance monitoring, and more particularly, to remote measurement system and method for pesticide fog distribution and drifting tendency in aerial pesticide application.

BACKGROUND

Pesticide drift in aerial pesticide application process is one of the important factors of pesticide pollution. Pesticide drift is physical movement of pesticide droplets or particles migrating from target area to non-target area in the sky under uncontrolled condition, during or after the aerial spraying process. Pesticide drift includes evaporation drift caused by volatilization of pesticide active ingredients, and windy drift, which mainly refers to the disappearance or re-settlement process of small droplets in the fog carried out of the target area by air flow. Droplets drift occurs invariably in the aerial spraying process; and pesticide drift occurs in all the spraying processes to a certain extent. Part of the pesticide fog in the aerial spraying may drift even a few kilometers away influenced by wind speed, tip vortex of the aircraft, flight altitude, flight speed and the like. The drift has serious effects on the pesticide application result and the environment: (1) the quantity of sprayed pesticide may be non-uniform when spraying by the uniform patrol spray manner, wherein some areas are applied with no pesticide but some other areas are applied with excessive pesticide, which causes the waste in pesticide and incompleteness in the result of pesticide application to some degree; (2) most of the pesticides are toxic or may generate toxic substances and greenhouse gasses after degradation. When the invisible gasification pesticide fog clouds drift out of the spray area, water, healthy vegetation, and forest may be polluted, greenhouse gasses can be generated, which may result in an immeasurable impact on the environment; and (3) pesticide fog may drift to residential areas unconsciously which could harm the health of residents. It may cause acute or chronic poisoning when a great quantity of pesticides gets into the human body through mouth, respiratory tract or skin.

In the current pesticide application operation, the fog droplets are sampled commonly by laying oil sensitive paper and water-sensitive paper on the ground (Visual and Image System Measurement of Spray Deposits Using Water-sensitive Paper, Applied Engineering in Agriculture. 2003, 19 (5): 549-552), and the spraying result is obtained based on pesticide fog coverage, droplet size, and other information calculated by image processing algorithms.

For the detection of the pesticide residing in the air, adsorptive process is usually used, i.e., extracting the air to be measured with a large flow gas sampler and feeding the extracted air through glass fiber filter film or adsorbent column constituted by adsorbent, then eluting the air with an organic solvent and concentrating the solvent to measure with an instrument. For example, Li Chengquan et al. have studied distribution of pesticide fog concentration and drift state by depositing a plurality of air samplers in different positions in a greenhouse with the method above (Research on the Distribution and Visualization of Pesticide Fog Concentration Field in Confined Spaces, Jiangsu University, a master's degree thesis, 2009).

Information like pesticide fog coverage and fog droplet size may be obtained by the method of laying oil-sensitive papers and water-sensitive papers on the ground, but the method has the following shortcomings:

(1) only the spray level of certain areas on the ground can be obtained, which cannot fully reflect the drift state of pesticide fog in the air;

(2) poor in effectiveness;

(3) the concentration and composition of the fog cannot be obtained; and (4) tiny droplets which suspend in the air all the time cannot be detected.

The pesticide in the air can be monitored with the gas sampling method, but the method has the following defects:

(1) only the collected gas is analyzed, which cannot reflect fully the distribution of the pesticide fog;

(2) the monitoring cannot be performed in real time and continuously;

(3) sampling and pre-treatment processes are complex, time-consuming, and laborious; and (4) the sampling and the analyzing for upper air pesticide fog are hard to be performed.

SUMMARY (A). The Technical Problem Sought to be Solved

The technical problem sought to be solved by the present invention is to provide remote measurement system and method for pesticide fog distribution and drifting tendency in aerial pesticide application which can show the drift of pesticide fog in the air completely and timely, and obtain the concentration and composition of the pesticide fog.

(B) The Technical Solutions

In order to solve the problems above, the present invention provides a remote measurement system for pesticide fog distribution and drifting tendency in aerial pesticide. The system comprises: a collection module for the collecting infrared radiation of a detected area, and guiding the infrared radiation into an optical module; an optical module for obtaining infrared imaging spectrum of the detected area distributed with pesticide fog clouds based on the incident infrared radiation, and sending the infrared imaging spectrum to a processing module; and a processing module for performing characteristic analysis on the infrared imaging spectrum, identifying the pesticide fog cloud, inverting concentration image of the pesticide fog cloud, and predicting drift tendency of the pesticide fog cloud based on the concentration image.

Preferably, the optical module further comprises a Michelson interferometer for splitting the incident infrared radiation into two beams of coherent light, and outputting the two beams of coherent light, wherein the optical paths of the two beams of coherent light have predetermined difference; and a plane array infrared detector for sensing the two beams of coherent light output by the Michelson interferometer.

Advantageously, the Michelson interferometer further comprises a beam splitter for splitting the incident infrared radiation into two beams of coherent light; and a mirror set including two stationary mirrors and one moving mirror for causing the predetermined difference in optical paths of said two beams of coherent light, wherein the moving mirror performs uniform motion.

Preferably, collection range of said collection module is adjustable.

The present invention also provides a remote measurement method for pesticide fog distribution and drifting tendency in aerial pesticide application. The method comprises the steps of:

S1. collecting infrared radiation of a detected area;

S2. obtaining infrared imaging spectrum of the detected area distributed with pesticide fog cloud based on the incident infrared radiation; and S3. performing characteristic analysis on the infrared imaging spectrum, identifying the pesticide fog cloud in the detected area, inverting concentration image of the pesticide fog cloud, and predicting drift tendency of the pesticide fog cloud based on the concentration image.

Preferably, step S2 further comprises:

S2.1 splitting the incident infrared radiation into two beams of coherent light, and outputting the two beams of coherent light, wherein optical paths of the two beams of coherent light have predetermined difference;

S2.2 sensing the output coherent light of the step S2.1 with a plane array detector;

S2.3 reading the spectral signal from each detecting unit of said plane array detector sequentially to form a plurality of interferograms; and S2.4 performing Fourier transform respectively on said plurality of interferograms to form an infrared imaging spectrum of the detected area distributed with said pesticide fog clouds.

Preferably, the infrared imaging spectrum comprises the infrared imaging spectrum of the background of the detected area and the infrared imaging spectrum of said pesticide fog cloud, wherein the background of the detected area are detected areas without the pesticide fog cloud.

Preferably, in the step S3, performing characteristic analysis on the infrared imaging spectrum with the infrared imaging spectrum of the background of the detected area subtracted.

Preferably, prior to the step S1, there is a step of obtaining the infrared imaging spectrum of the background of the detected area.

Preferably, the method further comprises the following step after the step S3:

S4. adjusting the spray area of the aerial pesticide application according to the predicted result of the step S3.

(C) The Beneficial Technical Effects

The system and method of the present invention may detect the pesticide fog of aerial pesticide application within a certain range (e.g. 1 km) in a non-contact manner. The distribution range and spreading tendency of the pesticide fog can be predicted based on concentration image of the pesticide generated in real time. The method of the present invention requires no person getting into the spray area and needs no sampling measurements, which overcomes the defects of the prior sampling method.

BRIEF DESCRIPTION OF THE DRAWINGS

FIG. 1 illustrates a schematic diagram of the remote measurement system for pesticide fog distribution and drifting tendency in aerial pesticide application according to one embodiment of the disclosure.

FIG. 2 illustrates a flow chart of the remote measurement method for pesticide fog distribution and drifting tendency in aerial pesticide application according to one embodiment of the disclosure.

DETAILED DESCRIPTION OF THE PREFERRED EMBODIMENTS

The present invention provides a remote measurement system and method for pesticide fog distribution and drifting tendency in aerial pesticide application, which will be described in detail in combination with the accompanying drawings and embodiments below.

Since gases or droplets with different chemical constituents have different fingerprinting spectrum characteristics in infrared region, components of the pesticide fog can be obtained by identifying the characteristics of the pesticide fog spectrum. Meanwhile, pesticides with different concentration have different absorption intensities; and the concentration of gaseous pesticide fog can be generalized by measuring the absorption peak intensity. With the principle above, the target gas can be identified from different backgrounds and interference, and the concentration of the gas cloud can be calculated quantitatively.

Pesticides have the characteristic of infrared absorption. Different types of pesticides have obvious absorption peaks at different wave bands. All the objects above the temperature of absolute zero emit infrared radiation. Taking the infrared radiation of the natural world as background, the specific band of the infrared radiation of environment would be absorbed when passing through the pesticide fog cloud.

Based on the principle described above, the present invention provides a remote measurement system and method for pesticide fog distribution and drifting tendency in aerial pesticide application based on infrared imaging spectrum. A model indicating the association between pesticide concentration and spectrum is built based on the infrared spectrum characteristics of pesticides; and each pixel in the imaging spectrum is processed and calculated, then a concentration image can be formed by joining the pixels together, wherein one pixel indicts the concentration of one point. The concentration distribution of the pesticide fog during spraying process can be obtained in real-time; and diffusion tendency of the pesticide fog can be predicted accordingly. Thus, fast, continuous, on-line monitoring can be realized which has high sensitivity and can be used at night.

As shown in FIG. 1, in accordance with one embodiment of the present invention, a remote measurement system for pesticide fog distribution and drifting tendency in aerial pesticide application comprises: a collection module 5, an optical module and a processing module.

The collection module 5 is used for collecting infrared radiation of a detected area, and guiding the infrared radiation into an optical module. The optical module is used for obtaining infrared imaging spectrum of the detected area distributed with pesticide fog cloud 1 based on the incident infrared radiation, and sending the infrared imaging spectrum to the processing module. The processing module is used for performing characteristic analysis on the infrared imaging spectrum, identifying the pesticide fog cloud 1 in detected area, inverting concentration image of the pesticide fog cloud 1, and predicting drift tendency of the pesticide fog cloud based on the concentration image.

Therein, the collection module 5 can be optical telescopes or cameras or the like. The optical module further comprises: a Michelson interferometer 2 for modulating infrared radiation, i.e., splitting the incident infrared radiation into two beams of coherent light with optical paths having measurable difference, and then outputting the two beams of coherent light, and a plane array infrared detector 3 for sensing the two beams of coherent light output by the Michelson interferometer 2. The plane array infrared detector 3 is comprised of a plurality of detecting units. Coherent lights interfere by time on each detecting unit of the plan array infrared detector 3. By reading signals from detecting units sequentially, the interferograms can be obtained. Perform the same collection for each detecting unit to get a plurality of interferograms. Each detecting unit corresponds to one spectrum. Perform Fourier transform for the interferograms to obtain an infrared imaging spectrum comprising a plurality of imaging spectra. This process is conducted by the processing module, which is preferably a computer 6.

The Michelson interferometer 2 further comprises: a beam splitter for splitting the incident infrared radiation into two beams of coherent light, and a mirror set including two stationary mirrors and one moving mirror for causing difference in optical paths of said two beams of coherent light, wherein the moving mirror performs uniform motion.

As shown in FIG. 2, in accordance with one embodiment of the present invention, the remote measurement method for pesticide fog distribution and drifting tendency in aerial pesticide application comprises the steps of:

S1: adjusting the collecting area (also called imaging range or detecting range) of the collection module, and collecting infrared radiation of a detected area;

S2: obtaining infrared imaging spectrum of the detected area based on the incident infrared radiation;

S3: performing characteristic analysis on the infrared imaging spectrum; identifying the pesticide fog cloud; inverting concentration image of the pesticide fog cloud; and predicting drift tendency of the pesticide fog cloud based on the concentration image.

Step S2 further comprises:

S2.1 Michelson interferometer splits the incident infrared radiation into two beams of coherent light by splitter; and two stationary mirrors and one moving mirror are used to obtain two beams of coherent light with different measurable light paths and then output them;

S2.2 through uniform motion of the moving mirror, coherent lights will interfere by time on each detecting unit of the plan array detector which senses coherent lights.

S2.3 reading spectral signals from detecting units of the plan array detector sequentially to obtain a plurality of interferograms;

S2.4 perform Fourier transform respectively on the plurality of interferograms to obtain a plurality of spectrum corresponding to a plurality of pixels of the infrared imaging spectrum diagram of the detected area distributed with pesticide fog cloud.

With quantitative measurement of infrared imaging spectrum, the concentration of each point in the pesticide fog cloud can be obtained, so as the concentration image, and thus the pesticide fog distribution in theaerial pesticide application can be monitored and drift and diffusion tendency of the pesticide fog can be predicted.

Infrared imaging spectrum of the detected area distributed with the pesticide fog clouds includes: infrared imaging spectrum of background 4 of the detected area and infrared imaging spectrum of the pesticide fog clouds 1, wherein the background 4 of detected area is detected areas without pesticide fog clouds 1. Accordingly, the method of the present invention, further comprises a step of obtaining the infrared imaging spectrum of background 4 of the detected area prior to step S1; and subtracting the imaging infrared spectrum of the background to obtain the infrared imaging spectrum of the pesticide fog clouds when monitoring the pesticide fog, i.e., performing the characteristics analysis on the infrared imaging spectrum which substracts the background 4 of the detected area in step S3.

Embodiment 1

In this embodiment, the detection range is 500 m, the pesticide spraying area is 300 m*300 m, and the pesticide is a type of methamidophos pesticide.

According to the method of the invention, this embodiment is performed as follows:

A1. depositing the collection module (camera) and the optical module in a location 500 m away from the spray area, wherein the optical module includes a built-in Michelson interferometer as well as a focal plane infrared detector;

A2. adjusting the lens to set its imaging area meeting with a range that the present embodiment requires. In the embodiment, the visual field angle should be adjusted to 2×arctan (150/500)=33.4° by adjusting the focal length of the lens.

A3. measuring theinfrared imaging spectrum of the background before pesticide spraying; obtain the infrared imaging spectrum of the spray area in real-time during pesticide spraying, and subtract the infrared imaging spectrum of the background from the infrared imaging spectrum of the spray area, hence obtaining the spectrum of the pesticide fog cloud . The spectrum has a range of 8 μm to 14 μm.

A4. executing measurement software on a computer to quantitatively measure each point in the spectrum with a characteristic wave band of 1051 cm−1 and 1272 cm−1 (which can be queried from the international standard spectrum library, or obtained through laboratory experiments) according to the spectral characteristics of methamidophos pesticide, and thereby obtain the concentration image.

A5. predicting the distribution range and diffusion tendency of the pesticide fog with the concentration image based on the prediction model.

Embodiment 2

In the present embodiment, the detection distance is 1000 m, pesticide spraying area is 200 m*200 m, and the pesticide is a type of methamidophos pesticide.

According to the method of the invention, this embodiment is performed as follows:

B1. depositing the collection module (optical telescope) and the optical module in a location 1000 m away from the spray area, wherein the optical module includes a built-in Michelson interferometer as well as a focal plane infrared detector;

B2. adjusting the optical telescope to set its imaging area meeting with a range that the present embodiment requires. In the embodiment, the visual field angle should be adjusted to 2×arctan (100/1000)=11.4°.

B3. obtaining infrared imaging spectrum of the spray area with a range of 8 μm to 14 μm in real-time during pesticide spraying.

B4. performing quantitative measurement on each point in the spectrum with a characteristic wave band of 1258 cm−1 and 1760 cm−1 according to the spectral characteristics of methamidophos pesticide, and thereby obtain the concentration image.

A5. predicting the distribution range and diffusion tendency of the pesticide fog with the concentration image based on the prediction model.

In the above two embodiments, the prediction model of the drift tendency of the pesticide fog can be generated based on the variation of the concentration image by time and the weather conditions. The model is used to predict where the pesticide fog will drift to then. Since the distribution range of the pesticide fog can be obtained in real time with the present invention, the variation tendency of the distribution range of the pesticide fog can be monitored continuously. If pesticide fog spreads eastward at a certain speed for 20 seconds, the time when it will reach a certain area in the east can be predicted. This is very important for the pesticide spraying, as the spray area can be adjusted if there is a prediction indicating the pesticide fog may flow out of the spray area in a certain time.

INDUSTRIAL PRACTICABILITY

The system and method of the present invention can be employed in monitoring and warning of the precise pesticide spraying process for the environmental protection department or agricultural workers to improve the effectiveness of pesticides application, and prevent damages on the environment and residential areas while saving the cost.

The invention claimed is:

1. A remote measurement system for pesticide fog distribution and drifting tendency in aerial pesticide application, characterized in that, the system comprises:
   a collection module for collecting infrared radiation of a detected area, and guiding the infrared radiation into an optical module;
   the optical module for obtaining infrared imaging spectrum of the detected area distributed with pesticide fog clouds based on the incident infrared radiation, and sending the infrared imaging spectrum to a processing module; and
   the processing module for performing characteristic analysis on the infrared imaging spectrum, identifying the pesticide fog clouds, inverting concentration images of the pesticide fog clouds, and predicting drift tendency of the pesticide fog clouds based on the concentration image.

2. A remote measurement system for pesticide fog distribution and drifting tendency in aerial pesticide application according to claim 1, characterized in that, the optical module further comprises:
   a Michelson interferometer for splitting the incident infrared radiation into two beams of coherent light, and outputting the two beams of coherent light, wherein the optical paths of the two beams of coherent light have predetermined difference; and
   a plane array infrared detector for sensing the two beams of coherent light output by the Michelson interferometer.

3. A remote measurement system for pesticide fog distribution and drifting tendency in aerial pesticide application according to claim 2, characterized in that, the Michelson interferometer further comprises:
   a beam splitter for splitting the incident infrared radiation into two beams of coherent light;
   a mirror set including two stationary mirrors and one moving mirror for causing the predetermined difference in optical paths of said two beams of coherent light, wherein the moving mirror performs uniform motion.

4. A remote measurement system for pesticide fog distribution and drifting tendency in aerial pesticide application according to claim 1, wherein collection range of said collection module is adjustable.

5. A remote measurement method for pesticide fog distribution and drifting tendency in aerial pesticide application, characterized in that, the method comprises the steps of:
   S1 collecting infrared radiation of a detected area;
   S2 obtaining infrared imaging spectrum of the detected area distributed with pesticide fog clouds based on the incident infrared radiation; and
   S3 performing characteristic analysis on the infrared imaging spectrum, identifying the pesticide fog clouds in the detected area, inverting concentration image of the pesticide fog clouds, and predicting drift tendency of the pesticide fog clouds based on the concentration image.

6. A remote measurement method for pesticide fog distribution and drifting tendency in aerial pesticide application according to claim 5, characterized in that, the step S2 further comprises:
   S2-1 splitting the incident infrared radiation into two beams of coherent light, and outputting the two beams of coherent light, wherein the optical paths of the two beams of coherent light have predetermined difference;
   S2-2 detecting the coherent light output in the step S2.1 with a plane array detector;
   S2-3 reading the spectral signal from each detecting unit of said plane array detector sequentially to obtain a plurality of interferograms; and
   S2-4 performing Fourier transform respectively on said plurality of interferograms to form infrared imaging spectrum of the detected area distributed with said pesticide fog clouds.

7. A remote measurement method for pesticide fog distribution and drifting tendency in aerial pesticide application according to claim 6, characterized in that, the infrared imaging spectrum comprises the infrared imaging spectrum of the background of the detected area and the infrared imaging spectrum of said pesticide fog clouds, wherein the background of the detected area are detected areas without the pesticide fog cloud.

8. A remote measurement method for pesticide fog distribution and drifting tendency in aerial pesticide application according to claim 7, characterized in that, in the step S3, performing characteristic analysis on the infrared imaging spectrumwith the infrared imaging spectrum of the background of the detected area subtracted.

9. A remote measurement method for pesticide fog distribution and drifting tendency in aerial pesticide application according to claim 8, characterized in that, prior to the step S1, there is a step of obtaining the infrared imaging spectrum of the background of the detected area.

10. A remote measurement method for pesticide fog distribution and drifting tendency in aerial pesticide application according to any one of claims 5-9, characterized in that, further comprises the following step after step S3:
   S4 adjusting the spray area of the aerial pesticide according to the predicted result of the step S3.

* * * * *